United States Patent
Slatkine

(10) Patent No.: US 6,293,940 B1
(45) Date of Patent: Sep. 25, 2001

(54) APPARATUS AND METHOD AS PREPARATION FOR PERFORMING A MYRINGOTOMY IN A CHILD'S EAR WITHOUT THE NEED FOR ANAESTHESIA

(76) Inventor: Michael Slatkine, 4009 Brookside Ave, Fairlawn, NJ (US) 07410

(*) Notice: Subject to any disclaimer, the term of this patent is extended or adjusted under 35 U.S.C. 154(b) by 0 days.

(21) Appl. No.: 08/978,230

(22) Filed: Nov. 25, 1997

Related U.S. Application Data

(63) Continuation of application No. 08/501,514, filed on Jul. 12, 1995, now Pat. No. 5,709,677.

(51) Int. Cl.[7] .................................................. A61B 18/18
(52) U.S. Cl. ................................ 606/17; 606/13; 606/19; 600/108
(58) Field of Search ............................... 606/10–19, 130; 607/88, 89; 600/108, 114, 200

(56) References Cited

U.S. PATENT DOCUMENTS

| | | | |
|---|---|---|---|
| 1,106,699 | * | 8/1914 | Carroll .................................. 600/200 |
| 3,884,236 | | 5/1975 | Kransnov . |
| 4,316,467 | * | 2/1982 | Muckerheide ........................... 606/9 |
| 4,387,952 | | 6/1983 | Slusher . |
| 4,441,485 | | 4/1984 | Reynolds . |
| 4,469,098 | | 9/1984 | Davi . |
| 4,566,453 | | 1/1986 | Kumanao . |
| 4,587,396 | | 5/1986 | Rubin . |
| 4,622,967 | * | 11/1986 | Schachar .............................. 600/200 |
| 4,672,969 | | 6/1987 | Dew . |
| 4,712,537 | * | 12/1987 | Pender .................................. 606/14 |
| 4,718,418 | | 1/1988 | L'Esperance . |
| 4,733,660 | | 3/1988 | Itzkan . |
| 4,768,513 | | 9/1988 | Suzuki . |
| 4,913,132 | * | 4/1990 | Gabriel ................................. 607/89 |
| 4,917,083 | | 4/1990 | Harrington . |
| 5,049,147 | * | 9/1991 | Danon ................................... 606/10 |
| 5,057,100 | * | 10/1991 | Lombardo .............................. 606/17 |
| 5,071,417 | | 12/1991 | Sinofky . |
| 5,112,328 | | 5/1992 | Taboada et al. . |
| 5,207,670 | | 5/1993 | Sinofsky . |
| 5,280,378 | | 1/1994 | Lombardo . |
| 5,336,217 | | 8/1994 | Buys et al. . |
| 5,360,424 | * | 11/1994 | Klopotek ................................. 606/4 |
| 5,364,390 | | 11/1994 | Taboada et al. . |
| 5,411,502 | | 5/1995 | Zair . |
| 5,776,144 | * | 7/1998 | Leysieffer et al. .................... 606/130 |

OTHER PUBLICATIONS

Sharplan 771 Microscan, Mar. 28, 1985, 3 pages.
Microprocessor—Controlled Scanning Micromanipulator for Carbon—Dioxide Laser Surgery, J. Neurosurgery 59, Dec. 1983, pp. 1098–1099.
Sharplan 771B Microscan, Lasers Industries (1985).
The Computerized Laser Scanner—Sharplan 775 Laser Industries.

(List continued on next page.)

*Primary Examiner*—Michael Peffley

(57) ABSTRACT

An apparatus and method for performing a myringotomy in a child's ear without the need for anaesthesia. A charge coupled device or television camera is aimed within a micromanipulator housing at a child's ear drum. The housing is retained to the ear, either with a fastener such as an adhesive or in a helmet, so that the housing moves with the movement of the child's head. A video image of the ear drum surface is displayed on a screen from signals transmitted from the camera device. A physician marks on the screen with an electronic pen pointer where the laser beam should be aimed at the ear drum surface. A microprocessor responds to this marking to determine the appropriate coordinates and instructs mirror control motors to rotate a scanning mirror in the path of the laser beam. The laser may be fired and its beam is directed by the scanning mirror to strike a desired location by passing through the housing attached to the child's ear without being affected by any sudden movement of the child's head.

22 Claims, 2 Drawing Sheets

OTHER PUBLICATIONS

Sharplan Swiftlase Flashcan, Jun., 1993.

Sharplan Lasers, Inc. Outgoing fax from Karen Amburgey, Oct. 19, 1994.

Reliant Technologies, Inc. Product News,Accu–Scan, Multi–Wavelength Laser Scanning System for CO2, Jan. 25, 1995, 3 pages.

"Aesthetic CO2 Laser System", literature, Aug. 1994, 2 pages.

Mihchael Slatkin, et al. "Instrumentation for Office Laser Surgery", Operative Techniques in Otolaryngology– Head and Neck Surgery, vol. 5,No. 4, Dec. 1994, pp. 211–217.

R. Rox Anderson, et al. "Selective Photothermolysis: Precise Microsurgery by Selective Absorption of Pulsed Radiation", Science, vol. 220, Apr. 29, 1993, pp. 524–527.

Andrew Blitzer, M.D., DDS, Laser Photocoagulation the Care of Patients with Osler—Rendu Disease Cooperative Techniques in Otolaryngology—Head and Neck Surgery, vol. 5,No. 4, Dec. 1994, pp. 274–277.

Arielle N.B. Kauvar, et al. "Laser Therapy for Cutaneous Vascular Lesions", Operative Techniques in Otolaryngology– Head and Neck Surgery, vol. 5,No. 4, Dec. 1994, pp. 250–258.

Sharplan 755/776/777 Microscan CO2 Surgical Laser Scanners, 4 pages.

Laser Industries Ltd. Announces Development of New Laser Scanner for Surgery, 5 pages.

Sharplan 771. General System Description, pp. 1–2 through 1–18.

Sharplan 775A/B. System Description, pp. 1–3 through 1–25.

Richard W. Maloney, MD "Laser Otology", Operative Techniques in Otolaryngology– Head and Neck Surgery, vol. 3,No. 2, Jun. 1992, pp. 74–83.

I. L. Med. Unilase product info. Brochure "The Proven Solution for Disk, Spinal Cord and Brain Microsurgery" (1993).

I. L. Med. Unilase product info. Brochure "The Proven Soluction for Otologic and Microlaryngeal Surgery" (1993).

Unilase A new CO2 Laser for Microsurgery, I.L. Med. Newsletter, vol. 1, No. 3, Spring 1991.

"New Laser for Microlaryngeal Surgery", I.L. Med. Newsletter, vol. 1, No. 1, Spring 1991.

S. George Lesinski, M.D et al. "Carbon Dioxide Lasers for Otosclerosis", Otolaryngologic Clinics of North America, vol. 26, No. 3, Jun. 1993.

I. L. Med. Unilase System Brochure (1993).

"Using a CO2 Laser During Conventional Microdiskectomy Shows Promise of Faster Recovery", I.L. Med Newsletter, vol. 1. No. 4, Spring 1991.

I.L. Med Magana Diskectomy Microreactor Set, Brochure.

"Palm Beach Gardens Medical Center First in Nation to Perform Advanced Laser Back Surgery", Press Release.

I.L. Med Unilase CO2 Laser Information Relating to Mounts, Balancing and Drapes.

I.L. Med Advertisement Suggesting Use of the CO2 Laser with the New Unilase.

* cited by examiner

APPARATUS AND METHOD AS PREPARATION FOR PERFORMING A MYRINGOTOMY IN A CHILD'S EAR WITHOUT THE NEED FOR ANAESTHESIA

This is a Continuation of application Ser. No. 08/501,514, filed Jul. 12, 1995, now U.S. Pat. No. 5,709,677.

FIELD OF THE INVENTION

The present invention relates generally to laser devices and biomedical applications thereof. More specifically, the invention relates to setting-up a laser-based system in preparation for performing a myringotomy in a child's ear without the need for anaesthesia.

BACKGROUND OF THE INVENTION

Myringotomy is a widely-performed procedure used in the treatment of "Otitis Media"-acute inflammation of the middle ear. Typically, it involves a surgical procedure whereby the surgeon performs a tiny incision of the eardrum in order to enable the drainage of fluids that accumulate in the eardrum. The incision in the eardrum must remain open and thus an open drainage ring is placed in the incision to prevent rapid healing and occlusion of the incision. This surgery is done under general anaesthesia.

Over the last few years surgeons performed myringotomy surgery using a pulsed $CO_2$ laser. The advantage of the pulsed $CO_2$ laser is its generation of thermal heat resulting in delayed healing of the incision of the eardrum. The incision remains open for approximately 3–6 weeks without the aid of an open drainage ring. Both the incision diameter and laser pulse time duration affect the incision healing time. Typically, the incision diameter is approximately 1 mm and the laser pulse time duration is 0.1 second at a 3–5 Watt power. This surgical technique is generally performed under anaesthesia, because the surgery uses a "defocused" beam that does not account for a child's unexpected movement.

There is a need to perform the myringotomy procedure more accurately without the need for anaesthesia. Moreover, there is a need to perform the myringotomy on the tympanic membrane of the child's ear drum such that any sudden, unexpected movement of the child's head will not adversely affect the carrying out of the myringotomy. The present invention, as described as follows, provides such an improved myringotomy procedure in children without anaesthesia.

SUMMARY OF THE INVENTION

One aspect of the invention relates to a method and apparatus suitable for carrying out laser surgery, such as for performing a myringotomy, but without the need for anaesthesia. The apparatus includes a viewing device and beam positioning device. The beam positioning device has an exit region from which emerges a laser beam.

Both the viewing device and the exit region of the beam positioning device are retained to move in unison with the target area that is to undergo the laser surgery. A viewing screen displays an image as viewed by the viewing device and, based on observation of the image, the physician decides where the laser surgery should take place and causes the beam positioning device to position the laser beam accordingly.

A common housing with two channels may be provided; one channel contains the viewing device and the entrance of the other is arranged to be neighboring the exit region of the beam positioning device. This housing may be retained with an adhesive strip to the ear of the patient or the housing may be defined by a helmet worn by the patient. Alternatively, the viewing device may be rigidly fixed to a handpiece, which is configured to permit passage of the laser beam.

BRIEF DESCRIPTION OF THE DRAWING

For a better understanding of the present invention, reference is made to the following description and accompanying drawings, while the scope of the invention is set forth in the appended claims.

DESCRIPTION OF THE PREFERRED EMBODIMENT

Figure 1:
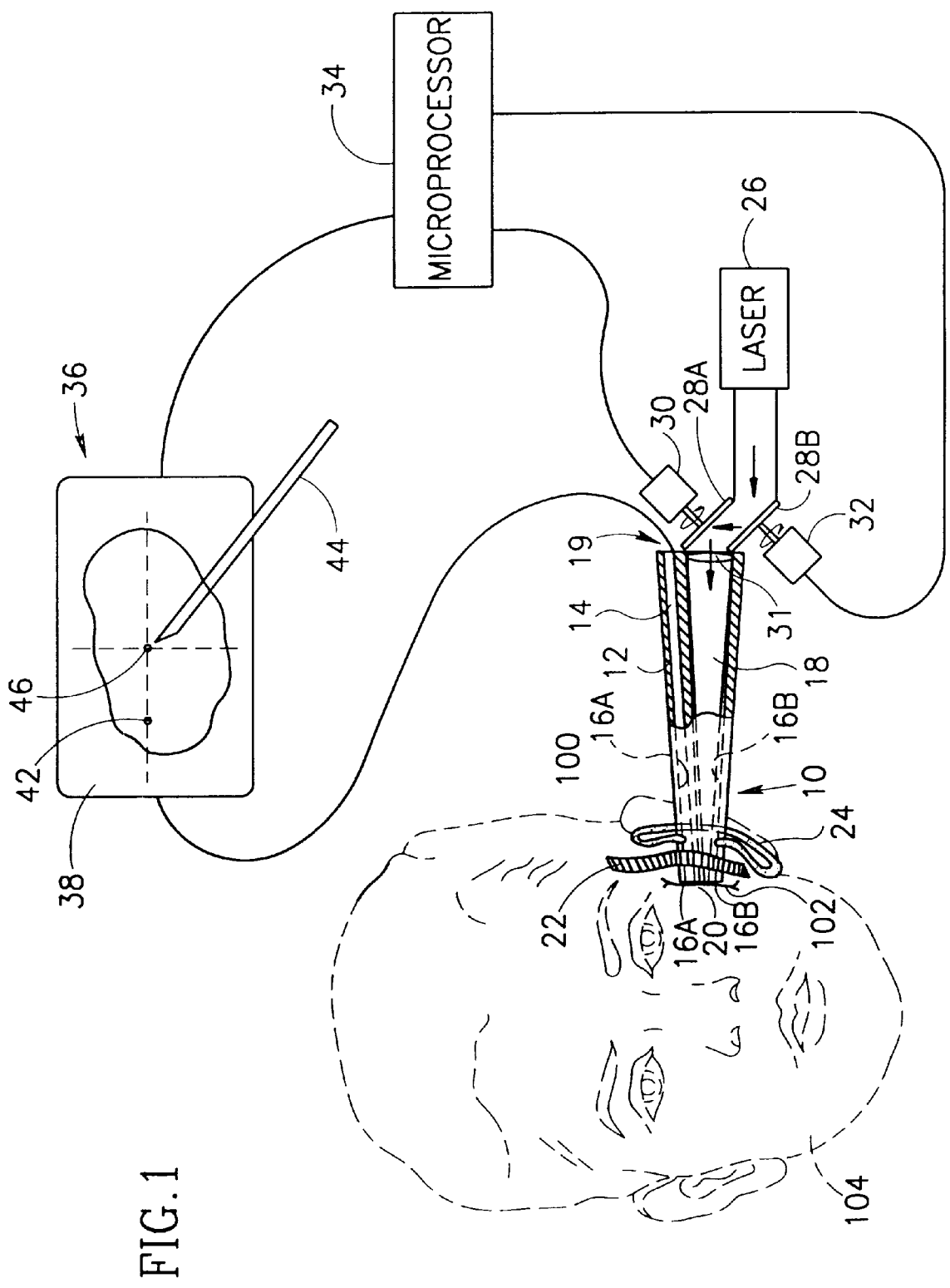
FIG. 1 is a schematic representation of the layout for treating myringotomy in children with a micromanipulator adhered to a child's head in accordance with the invention.

FIG. 1 shows a micromanipulator 10, which is a type of small, rigid, operating otoscope. It has a housing 12 that has through-going channels 16A, 16B. A viewing device 14 is within the channel 16A and rigidly affixed to the housing 12. A laser beam 18 emerges from a lens 31 in an exit region 19 to pass through the other channel 16B. This exit region 19 neighbors the entrance to this other channel 16B.

The housing 12 has a forward end 20, which is preferably open or transparent to permit viewing and lasing therethrough. The housing 12 is inserted into the patient's ear 100 so that the forward end 20 faces the ear drum 102. An adhesive strip 22 adheres the housing 12 to the patient's head 104 and a band 24 is wrapped around the ear in the manner shown in FIG. 1. The housing thus moves in unison with the patient's head and thereby with the tympanic membrane area to be lased.

A movable scanner mirror 28A is rotatable as movable scanner mirror 28B is movable about one axis in response to actuation of a control motor 30 and about another axis perpendicular to the one axis in response to actuation of another control motor 32. These motors 30, 32 are selectively actuated to rotate the mirrors 28A, 28B into a desired orientation and stopped in response to instructions from a microprocessor 34.

A video monitor 36 with a viewing screen 38 displays the image 40 of a tympanic membrane of the ear drum. The image 40 arises from signals transmitted from the viewing device 14. In the image 40, the current striking location 42 of the laser beam may become visible to assist the physician in determining from where the striking position is to be moved.

One way to make the current striking location 42 visible in the image 40 is to fire a visible laser beam at the location where firing the laser for performing the laser surgery is to strike. This could be done with a pilot laser appropriately positioned to fire such a beam.

Another way to make the current striking location 42 visible in the image 40 is to observe the changes in infrared temperature emissions on the tympanic membrane of a short burst of the invisible laser beam that is to be used to perform the laser surgery. The burst preferably is of shorter duration than and not as strong as the laser bursts used for the laser surgery, but sufficient for a noticeable impact on the image of the tympanic membrane on the viewing screen.

An electronic pen pointer 44 is used to mark a target location 46 on the screen 38 that corresponds to a target area to be lased as determined by a physician or other medical personnel by contacting the viewing screen 38 accordingly. Either the screen 38 or electronic pen pointer 44 is responsive to such contact to provide coordinate information of this target location 46 to the microprocessor 34.

The current striking location 42 must become known to the microprocessor 34 to effect the appropriate calculations for instructing the mirror control motors 30, 32 to move and rotate the scanner mirror 28 accordingly. This could be done by sending the microprocessor 34 coordinate information on the current striking location 42 in response to the physician using the electronic pen pointer 44 to contact the viewing screen 38 at the current striking location 42 as it appears in the image 40. Of course, the microprocessor 42 will need to be programmed to detect whether the physician is marking location 42 or target location 46. The program may be such that coordinate information relating to location 42 always precedes that relating to the target location 46 and the physician could be so prompted through an appropriate message on the viewing screen 38.

As an alternative, the microprocessor may ascertain the current striking location 42 on its own based on the relative position of the scanner mirror 18 or on previously determined coordinate information stored in memory that represent the current striking location. In this manner, the physician need only mark the target location 46 corresponding to where the surgery is to be performed.

After making such a comparison of coordinate information as between locations 42 and 46, the microprocessor 24 instructs the mirror control motors 30, 32 to rotate the scanner mirrors 28A, 28B to the appropriate relative orientation. Thus, upon firing of the laser 26 thereafter, the beam 18 that is emitted strikes the scanner mirror 28A, 28B which in turn deflects the beam in dependence upon the screen's relative angular inclination to the desired target area on the tympanic membrane that corresponds to that of the target location 46 in the image 40.

Figure 2:
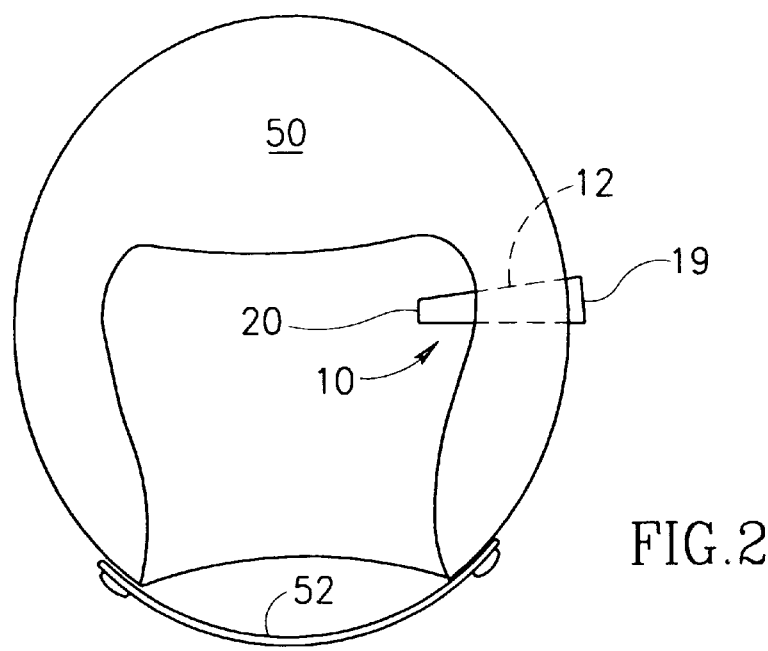
FIG. 2 is a schematic representation of the micromanipulator of FIG. 1 except that it is within a helmet.

FIG. 2 shows a helmet 50 used to retain the micromanipulator 10 in position on the patient's head. The forward end 20 of the micromanipulator is positioned to face the tympanic membrane of the ear drum as was the case in FIG. 1. If the micromanipulator 10 must be inserted further into the ear itself after the helmet is put on, this may be done manually by the physician while viewing the insertion on the viewing screen 38. The helmet may have a passage that defines the channels 16A, 16B of the housing 12; in effect, the helmet could be the housing itself.

If the patient could be injured if the helmet is removed while the micromanipulator 10 extends into the ear, then safety precautions can be taken to prevent this from happening. For instance, the fastening and unfastening of a chin strap 52 could trigger whether the micromanipulator can be inserted into the ear (i.e., only if the chin strap is fastened) or the immediate withdrawal of the micromanipulator 10 under spring bias (i.e., if the chin strap is unfastened).

Figure 3:
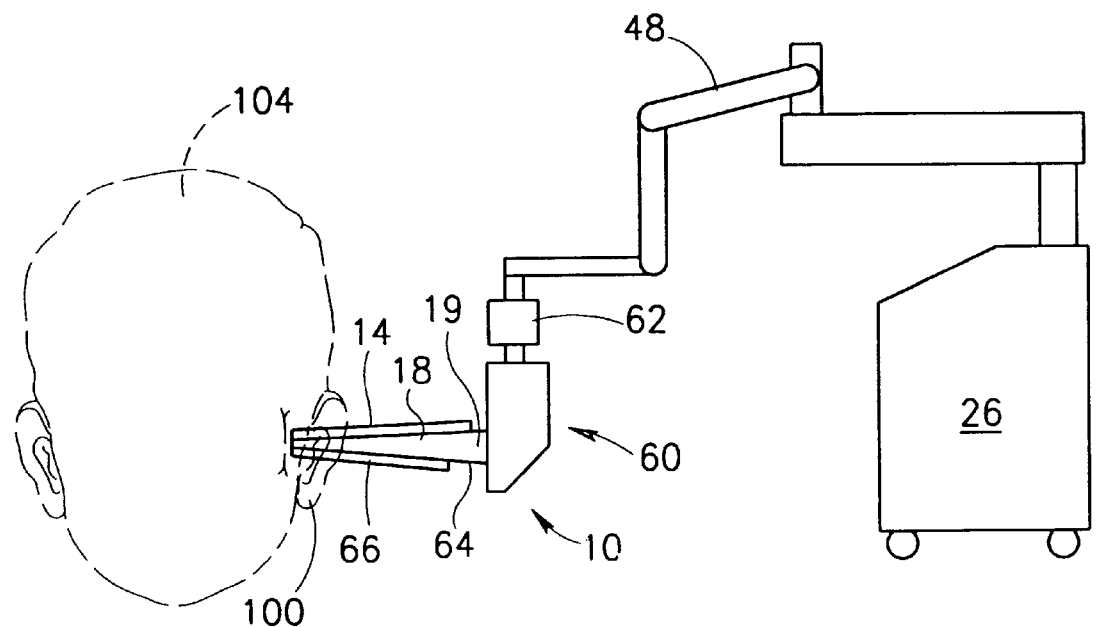
FIG. 3 is a laser apparatus suited for use in accordance with the invention of FIGS. 1 or 2.

Referring to FIG. 3, the articulated arm 48, which is between the laser 26 and the micromanipulator 10, is jointed to permit the micromanipulator 10 to be moved relative to the laser 26. The articulated arm 48 is constructed in a conventional manner, such as is disclosed in U.S. Pat. No. 5,411,502 (the '502 patent), entitled SYSTEM FOR CAUSING ABLATION OF IRRADIATED MATERIAL OF LIVING TISSUE WHILE NOT CAUSING DAMAGE BELOW A PREDETERMINED DEPTH, issued to Eliezer Zair on May 2, 1995, which is incorporated herein by reference. The arm 48 may be hollow to allow extension therethrough of fiber cable, waveguides or other laser transmitting media to convey the laser beam emitted from the laser 26 to the micromanipulator 10. Thus, sudden, unexpected movements of the head 104 will be compensated by the articulated arm 48 moving in conjunction with the micromanipulator 10 and thereby with movement of the head.

The micromanipulator 10 may include a joystick 60 to enable the surgeon to manipulate the viewing device within the housing 12 as desired. The scanner mirrors 28A, 28B and mirror control motors 30, 32 of FIG. 1 may be within enclosures 62. For the sake of brevity, the viewing screen 38 and the microprocessor 34 of FIG. 1 are not shown in FIG. 3, but they may be remote from or attached to the unit shown in FIG. 3.

Also, the common housing 12 of FIG. 1 is not shown and could be omitted; instead, the viewing device 14 could be rigidly attached, e.g., with an adhesive, to a handpiece 64 through which passes the laser beam 18 in the manner shown in FIG. 3. The handpiece 64 could be inserted into the channel 16B of the housing 12 of the embodiment of FIGS. 1 and 2.

The entire treatment is performed independent of child head movement. If the child's head happens to move when the laser is being aimed or fired, the movement will not necessitate manual re-aiming as was done conventionally because the micromanipulator moves with the movement of the child's head. In addition, the treatment should not be much longer or more annoying for the patient (child), who conventionally is diagnosed with an otoscope without anaesthesia. The healing time should be about six weeks.

The individual components mentioned are conventional, except for the shape of the housing 12. The housing may be made from any nonreflective material to avoid creating deflections of the beam passing through its chamber 16B. The length of the chamber 16B should be of a sufficient length to allow the beam to reach the target area with a desired spot size. The chamber may be configured to facilitate attaining the desired dimension. The viewing device 14 is exemplified by a charge coupled device or television camera.

The video monitor 36 is conventional, but any conventional viewing screen such a flat screen, projection screen, etc. may be used as an alternative, preferably passing coordinate information to the microprocessor 34 as desired. If the screen is touch sensitive, the physician could simply touch the screen at the appropriate target location and coordinate information would be generated and processed by the microprocessor 34.

Any conventional marking technique for sending coordinate information to the microprocessor may be used instead of the electronic pen pointer. For instance, a keyboard terminal or other data entry device such as a mouse, joystick or track ball could be used that move a cursor to the appropriate location on a monitor screen. Alternatively, a light emitting pointer device could be used where the monitor screen is photosensitive. These types of devices may be considered marking devices since they are used to identify or mark a location on a screen. Once such a location is marked, coordinate information is transmitted to the microprocessor for further processing.

In addition, the marking device (e.g., the electronic pen pointer 44) and the microprocessor 34 may be dispensed with entirely. For instance, by observing the image 40 on the viewing screen 38 alone, the observer can see the current striking location 42. By moving a joystick 60 (see FIG. 3), which is connected to allow manipulation of the laser beam (in the manner taught in the '502 patent or the Sharplan 710 micromanipulator), the aiming of the laser beam and thereby the current striking location 42 can be moved to the target location 46 that corresponds to the desired target area in the tympanic membrane to be lased. Such movement of the current striking location 42 is watched on the viewing screen 38. Once the current striking location 42 reaches the target location 46, the laser 26 may be fired to commence the laser surgery on the corresponding target area. One suitable type of laser 26 is a $CO_2$ laser emitting a defocussed beam. Preferably, the spot size is 1 millimeter and the power level is 5 watts with a time duration of 0.1 seconds. Another suitable type is a Nd:YAG laser with a pulsed energy of ½ joule, with the same 1 millimeter spot size and fired for one or two pulses. Still another suitable type of laser 26 employs a flashscanner, such as that of a Sharplan 710 micromanipulator, to provide better control of the hole diameter since the beam emitted is focussed, preferably making a spiral pattern as it scans the target area.

Examples of laser disclosures suitable for making a spiral pattern and/or a lissageous pattern to serve as the laser 26 of the present application: the '502 patent and the pending U.S. patent application Ser. No. 08/358,386, entitled METHOD AND APPARATUS FOR APPLYING A LASER BEAM TO A WORKING SURFACE, PARTICULARLY FOR ABLATING TISSUE, and filed Dec. 19, 1994, which are incorporated herein by reference.

While carrying out the laser surgery, it may be medically important to know when the tympanic membrane has been penetrated. As soon as this is known, the lasing process can cease to save the posterior section of the middle ear from unnecessary laser radiation (although the laser beam is expected to be unfocussed and not damaging).

Upon observation of the image 40 as seen on the viewing screen 38, the physician can watch the lasing of the hole through the membrane to know when the tympanic membrane of the ear drum has been penetrated to permit the escape of excess fluid. When such penetration arises, there will be a noticeable change in the observed characteristics at the target area as it appears on the viewing screen 38.

For instance, infrared temperature emissions from the target area in the tympanic membrane from use of an the surgical laser beam vary depending upon whether the tympanic membrane has been penetrated or not. If a visible pilot laser beam is used to check the hole penetration, such as that from a He-Ne pilot laser, the reflected power level of the beam varies depending upon whether the tympanic membrane has been penetrated or not. In either case, penetration is readily observed on the viewing screen 38.

As an alternative to observing for changes to check penetration, a sensor 66 (see FIG. 3) may be used which, when it senses penetration of the tympanic membrane, shuts off the laser automatically. For instance, a sensor of reflected power level could be used where a He-Ne pilot laser is fired at the hole penetration. A sensor of infrared radiation emissions could be used where a laser suited for performing the laser surgery is fired at the hole penetration.

In accordance with the preferred embodiment, the beam positioning device or scanner may include the scanner mirror 28, the mirror control motors 30, 32 and the exit region 19. In addition, the beam positioning device may further include the microprocessor 34, marking device and transmission of coordinate information from the viewing screen 38.

The mirror control motors 30, 32 may be any other form of drivers for the scanner mirrors 28A, 28B whether driven electrically, pneumatically or hydraulically. The microprocessor 34 may instead be any other type of controller that performs the same functions and may be in the form of other integrated circuitry or its analog counterpart.

The present invention is advantageously used on children because securing the housing to the child's head ensures that the housing moves in unison with movements of the child's head instead of independent of it. The present invention could also be used on adults or animals, particularly useful in those cases where the head is subject to sudden, uncontrolled movements such when the patient suffers from certain kinds of nervous disorders.

In addition, the present invention has application to other forms of treatment in the ear other than for treating myringotomy and may be directed at other regions of the ear other than the tympanic membrane. The present invention has application for treatment of the eye, mouth, nose, skin and other parts of the head where the risk of unexpected, sudden head movement during laser surgery is detrimental. Indeed, the present inventive apparatus may be used to treat any external part of the body.

While the foregoing description and drawings represent the preferred embodiments of the present invention, it will be understood that various changes and modifications may be made without departing from the spirit and scope of the present invention.

What is claimed:

1. An apparatus suitable for preparing to perform laser surgery on a subject without the need for anesthesia, said apparatus comprising:

a housing:

an imaging device mounted within said housing and aimed at a desired target area.;

a beam positioning device in operative communication with said imaging device, said beam positioning device mounted to said housing to direct a laser beam to travel along a path through said housing to strike the desired target area, said beam positioning device being movable to alter said path that the laser beam is directed to travel; and a retainer that secures said housing to said subject in a relative position with respect to the desired target area so that said housing moves in unison with and in response to movement of the desired target area to maintain said relative position throughout said movement.

2. An apparatus as in claim 1, wherein said retainer is selected from the group consisting of an adhesive material, a band, both an adhesive material and a band, and a helmet defining said housing.

3. An apparatus as in claim 1, where said imaging device includes a device selected from the group consisting of a charge coupled device and a television camera.

4. A method useful in preparing to perform laser surgery on a subject without the need for anesthesia, said method comprising of steps of:

imaging a target area suited for performing laser surgery with an imaging device mounted within a housing and aimed at the target area to obtain at least one image;

retaining the housing on said subject to move in unison with and in response to movement of the target area to maintain a relative position of said housing relative to said target area throughout said movement; and utilizing said image to adjust a beam positioning device in operative communication with said imaging device, so that upon firing of a laser that emits a laser beam, the laser beam travels along a path through said housing and passes through said housing to strike the target area, the beam positioning device being mounted to said housing.

5. A method as in claim 4, wherein the step of retaining includes adhering the housing to a head so that the viewing device is aimed at an ear drum.

6. An apparatus suitable for preparing to perform laser surgery on a subject without the need for anesthesia, said apparatus comprising:

an imaging device aimed in a direction to pick up an image of a target area;

a screen responsive to said imaging device for displaying images as viewed by said imaging device;

a beam positioning device in operative communication with said viewing device, said beam positioning device being movable to alter a path traveled by a laser beam aimed to strike the target area, said beam positioning device having an exit region from which the beam emerges to leave said beam position device prior to striking the target area; and a retainer that retains on said subject, said imaging device and said beam positioning device at a relative position of the imaging device and exit region of said beam positioning device with respect to a target area so that both the imaging device and exit region move in unison with and in response to movement of the target area and so that said relative position is maintained throughout said movement.

7. An apparatus as in claim 6, wherein said screen provides coordinate information of a desired location that corresponds to the target area, said beam positioning device being responsive to said coordinate information to alter the path traveled by the laser beam.

8. An apparatus as in claim 7, further comprising a marking device, said screen being responsive to said marking device to provide said coordinate information.

9. An apparatus as in claim 6, wherein said imaging device includes a device selected from the group consisting of a charge coupled device and a television camera.

10. An apparatus as in claim 6, wherein said beam positioning device includes a microprocessor and a scanner, said microprocessor providing instructions for moving said scanner.

11. An apparatus as in claim 10, wherein said scanner includes a mirror and mirror control drivers, said mirror being arranged in a path that the laser beam will travel, said mirror control drivers responding to said instructions from said microprocessor to position said mirror so that said laser beam strikes the target area.

12. An apparatus as in claim 6, wherein the retainer is selected from the group consisting of an adhesive material, a band, and a helmet.

13. An apparatus as in claim 6, wherein the laser beam has a power level and reflects off the target area, further comprising a sensor arranged in a path traveled by the reflected laser beam and that detects changes in the power level reflected off the target area, said sensor indicating when the power level being reflected is such that the penetration of the target area has occurred.

14. An apparatus as in claim 6, wherein infrared radiation emissions emanate from the target area in response to the laser beam striking the target area, further comprising a sensor arranged in a path traveled by the infrared radiation emissions and that detects changes in the infrared radiation emissions from the target area, said sensor indicating when the infrared radiation emissions are such that the penetration of the target area has occurred.

15. A method suitable for preparing to perform laser surgery on a subject without the need for anesthesia, comprising the steps of:

aiming an imaging device towards a desired target area suitable for performing laser surgery;

displaying an image indicative of the desired target area on a viewing screen;

adjusting a beam positioning device in operative communication with said viewing device to alter a path that a laser beam emitted from a laser is to travel, the beam positioning device having an exit region through which emerges the laser beam upon leaving the beam position device; and retaining on said subject, said imaging device and said beam positioning device so as to maintain a relative position of the imaging device and the exit region with respect to the target area so that both the imaging device and exit region of said beam adjusting device move in unison with and in response to movement of the target area and so that said relative position ins maintained through said movement.

16. A method as in claim 15, wherein the step of adjusting includes actuating mirror control motors to alter a relative position of a mirror.

17. A method as in claim 15, wherein the screen provides coordinate information, the step of adjusting being responsive to the coordinate information to alter the path.

18. A method as in claim 17, further comprising the step of marking the screen, said screen being responsive to the step of marking to provide the coordinate information.

19. A method as in claim 15, wherein the image is indicative of a tympanic membrane of the ear drum containing the desired target area.

20. A combination that includes the method as in claim 15 in combination with performing laser surgery which comprises the steps of watching the image on the viewing screen while firing a laser repeatedly to generate the laser beam that strikes a tympanic membrane.

21. A combination as in claim 20, wherein the step of watching includes observing changes over time in the appearance of the target location within the image that signify that penetration of the tympanic membrane has taken place and then ceasing the firing to avoid unnecessary lasing after penetration is realized.

22. A combination as in claim 21, wherein the step of watching includes watching for changes in any one of reflected power levels and infrared temperature emissions.

* * * * *